United States Patent [19]

De Bellis et al.

[11] Patent Number: 5,649,967
[45] Date of Patent: Jul. 22, 1997

[54] SAFETY ELEMENT TO PERMANENTLY ASSURE THE ELECTRIC RELIABILITY OF PULSE TRANSMITTING LEADS UTILIZED IN CARDIAC PACEMAKERS FOR THE ELECTRIC STIMULATION OF THE HEART

[75] Inventors: Ferruccio De Bellis, Rome; Enzo Borghi, Budrio, both of Italy

[73] Assignee: P.A. & M. S.p.A., Rome, Italy

[21] Appl. No.: 399,905

[22] Filed: Mar. 7, 1995

[30] Foreign Application Priority Data

Mar. 10, 1994 [IT] Italy ............... RM94A0130

[51] Int. Cl.⁶ ........................... A61N 1/372
[52] U.S. Cl. ........................ 607/9; 607/122; 607/63
[58] Field of Search ................ 607/37, 63, 122, 607/148, 9; 128/772; 439/909

[56] References Cited

U.S. PATENT DOCUMENTS

| | | | |
|---|---|---|---|
| 4,466,690 | 8/1984 | Osypka | 339/272 A |
| 4,943,289 | 7/1990 | Goode et al. | 606/1 |
| 5,005,587 | 4/1991 | Scott | 607/122 |
| 5,405,372 | 4/1995 | Gilljam et al. | 607/119 |

*Primary Examiner*—William E. Kamm
*Assistant Examiner*—Kennedy J. Schaetzle
*Attorney, Agent, or Firm*—DeLio & Peterson, L

[57] ABSTRACT

Safety element intended to assure in time the electric reliability of pulse transmitting leads, comprised in apparatus for the electric stimulation of the heart (pacemaker) and consisting of a main metallic coil of tubular structure delimiting an inner bore, covered by an insulating sheath, which safety element comprises a flexible lead formed by one or more wires coiled in tight turns or intertwined and provided with a rounded head for making it easier the introduction of the safety element in the bore of the main metal coil of the pulse transmitting lead.

4 Claims, 3 Drawing Sheets

SAFETY ELEMENT TO PERMANENTLY ASSURE THE ELECTRIC RELIABILITY OF PULSE TRANSMITTING LEADS UTILIZED IN CARDIAC PACEMAKERS FOR THE ELECTRIC STIMULATION OF THE HEART

This invention relates to the field of cardiac pacemakers or PM implantation for the electric stimulation of the heart in patients without natural stimulation or suffering from insufficient natural stimulation.

As is known to experts, such an implant includes a PM inserted in a sub-cutaneous pocket in the patient's chest, which PM generates the electric stimulation pulses, and a so called electrode catheter, namely a pulse transmitting lead, extending from the PM to the heart that carries to the latter the stimulation pulses.

For this purpose, when firstly implanting the PM, the pulse transmitting lead is inserted in the selected vein, usually the cephalic vein, through an opening surgically prepared; the pulse transmitting lead is then pushed along the subclavian vein, anonymous vein and cava vein until the distal tip thereof reaches the right ventricle of the heart to which the pulse transmitting lead is anchored or screwed by appropriate means.

Pulse transmitting leads have generally a coiled structure, comprising an external insulating sheath and an internal coil consisting of wires made of a special metal alloy having a high electric conductivity, spirally wound in tight coils to form an internal bore.

This tubular structure is essential for completing the installation of the pulse transmitting lead since as a matter of fact coils are, by their nature and construction, highly flexible, and accordingly the introduction of the pulse transmitting lead along the above-mentioned veins would be impossible; the operation is then carried out by temporarily increasing the rigidity of the pulse transmitting lead.

The increase in rigidity is obtained by introducing in the bore of the coil a thin, solid metallic wire, called mandrel, of sufficient rigidity having the same length of the pulse transmitting lead, the mandrel is removed upon completion of the operation when the distal end of the pulse transmitting lead reaches the heart ventricle to which it is fixed; after this operation is accomplished the pulse transmitting lead is kept in place to carry out its function.

After a certain period of time, as known to expert in this field, it is necessary to replace the pacemaker and on that occasion the functional status of the pulse transmitting lead is checked by means of intra-operatory tests aimed at verifying whether the physical conditions thereof are satisfactory and no replacement is required.

Said intra-operatory tests allow one to measure the circulating current (Ic), the threshold current (Is) and the safety factor Fs where: Fs=Ic/Is, together with the electric check-up of the pulse transmitting lead.

Although these tests are always carried out with maximum accuracy, they do not allow the presence of cracks or micro-fractures to be detected which cracks may have occurred in the metal structure of the coil of the pulse transmitting lead which, in time, may lead to the fracture of the coil, interruption of its electric continuity and consequently the danger of interrupting the electric stimulation of the heart.

The micro-fractures or cracks may occur more easily in the lengths of the pulse transmitting lead in correspondence of which the same is narrowly bent and therefore mechanically stressed, i.e. in the length that comes out of the PM in the sub-cutaneous pocket, in the bend formed in the passage from the anonymous vein to the superior cava vein and, finally, in the bend formed when entering the atrium.

Unfortunately it is not sure that micro-fractures or cracks already existing in the pulse transmitting lead are detected by the electric tests as they do not always affect the values measured by such tests.

The response of tests can only confirm that, at the measurement time, there were no electrical interruptions but they do not ensure the future electric continuity of the pulse transmitting lead if microfractures or cracks are already present.

Accordingly it is the object of the invention to provide a novel auxiliary lead element which is constructed and located in such a way that the electric continuity of the pulse transmitting lead is assured for a long time thereafter.

According to the invention, the problem of constantly assuring the electric continuity of a pulse transmitting lead that has remained implanted for a long time, is solved by utilizing an additional safety element, extremely flexible and so sized to be exactly fitted and accommodated in the central passage or bore of the existing pulse transmitting lead, comprising a similar constructed coil or a small cable of intertwined wires.

As mentioned, said passage, during the first implantation, accommodates the mandrel utilized to increase the rigidity of the coil structure.

It is important to point out that according to the invention the diameter of both the additional coil or the intertwined wires, shall be such that the external surface thereof is always in contact with the internal surface of the coil of the pulse transmitting lead originally installed.

The invention will now be described in detail with reference to the attached drawings wherein.

Figure 1:
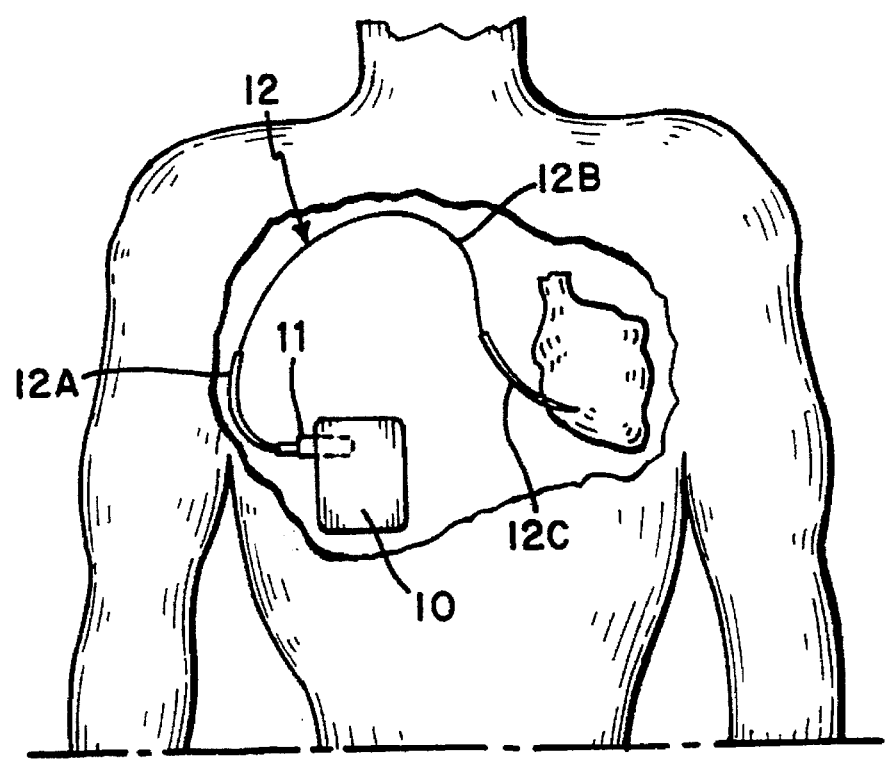
FIG. 1 is a general view of a device for the assisted cardiac stimulation as implanted in a patient.

Looking at FIG. 1 it is possible to identify the positions of PM 10 and the length of pulse transmitting lead 12 that connects the former to the patient's heart HT to which the stimulation pulses have to be applied.

As shown by thickened lengths of line 12A, 12B and 12C, pulse transmitting lead 12 is bent very narrowly in three crucial points representing the lengths of pulse transmitting lead 12 subject to maximum mechanical stress wherein the formation of cracks is more likely to take place. The invention is aimed at preventing the severe consequences that the formation of such cracks may bring about.

Figure 2:
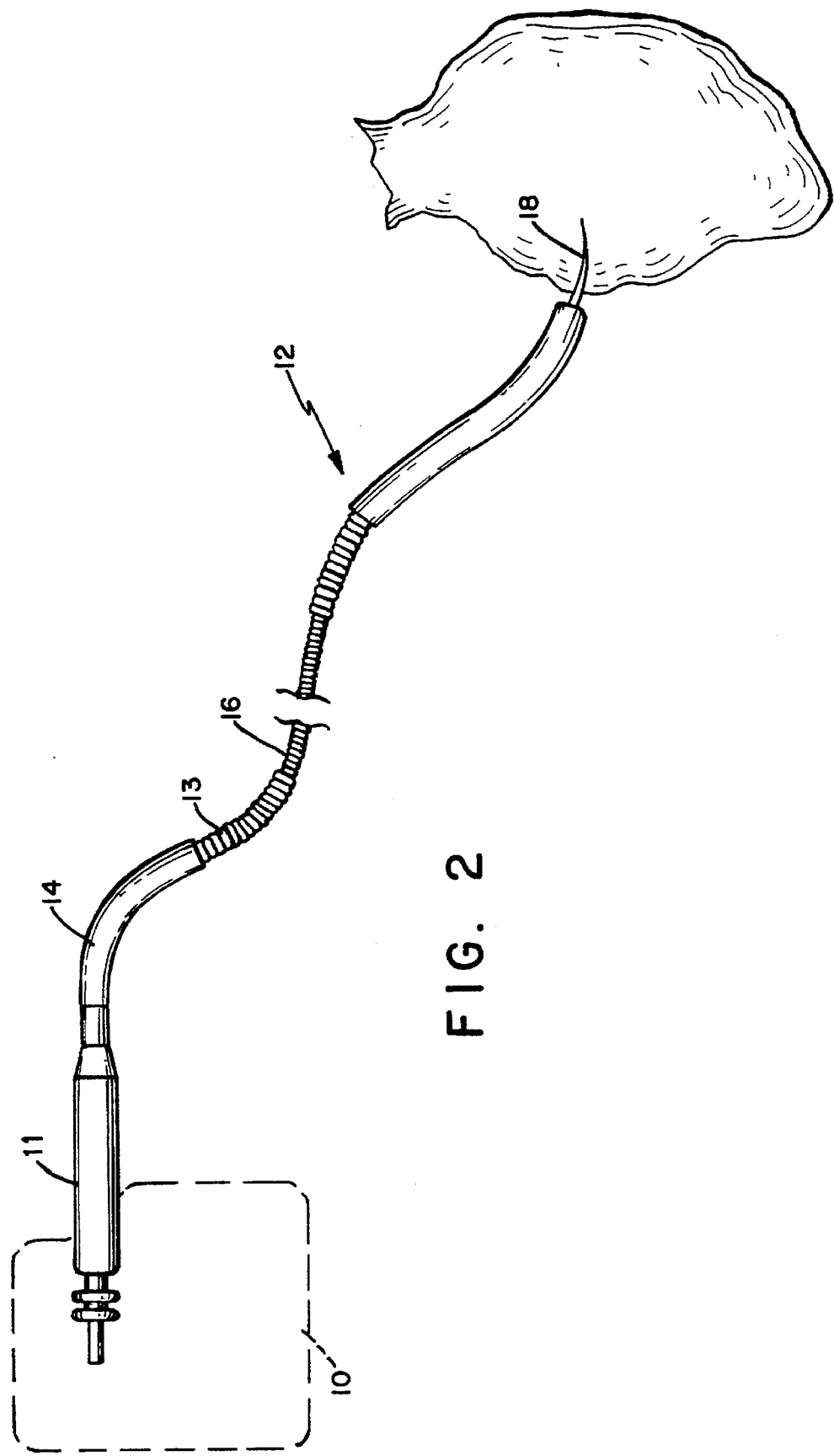
FIG. 2 shows in more detail the elements illustrated in FIG. 1.

Referring to FIG. 2, the pulse transmitting lead shown is of a conventional type. It has a contact pin-jack 11 for insertion in the PM and it consists of coil 13, made of a special metal alloy with optimal electric conductivity, covered with an insulating sheath 14. Coil 13 has a tubular construction and therefore presents a bore 15 all along its length.

Figure 4:
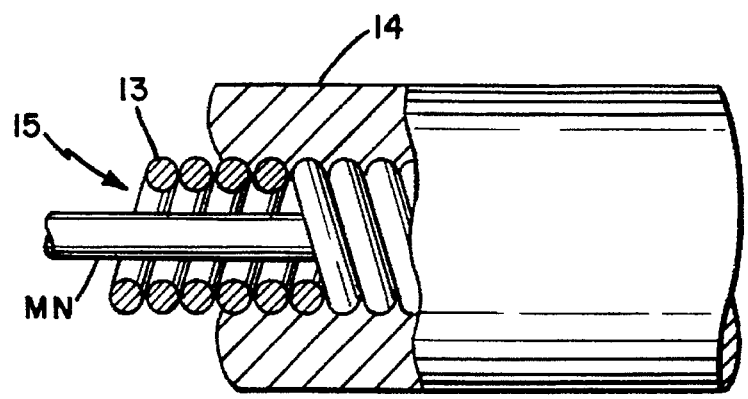

Inside this bore, during the introduction of the pulse transmitting lead into the selected veins, mandrel MN is inserted to increase the coil rigidity, as already mentioned and shown in FIG. 4.

According to the invention, at the first replacement of PM 10, the safety element 16 of the present invention is fitted into bore 15 of coil 13 of pulse transmitting lead 12. The safety element is inserted into bore 15 through a hole drilled in pin-jack 11. The safety element 16 is shown in its first embodiment in FIG. 5, formed as a coil similar to main coil 13.

As it will be easily understood, element 16, is positioned in bore 15 and connects PM 10 to the distal end 18 of pulse transmitting lead 12. Pulse transmitting lead 12 is fixed to the right ventricle of the heart HT and the safety element 16 has its external surface in contact with the internal surface of bore 15, so assuring that the signals of the pacemaker can reach the heart even in the event of a rupture of main coil 13.

Figure 6:
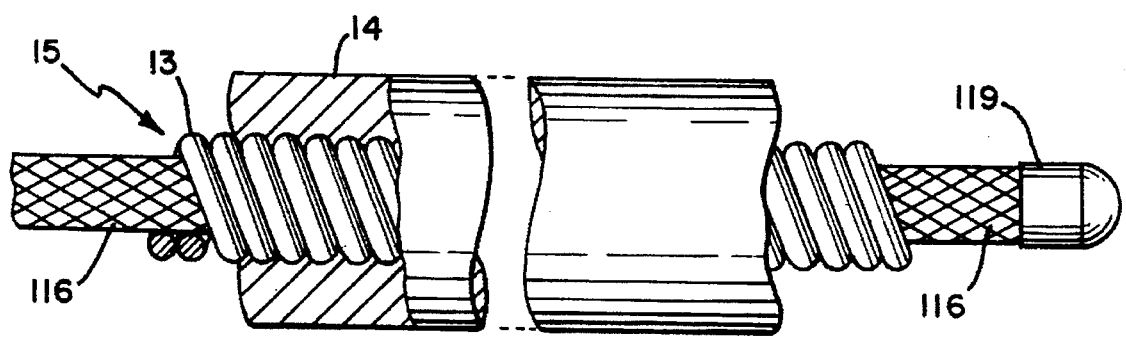
FIG. 6 is a similar section of a second embodiment of the invention similarly provided with a rounded head.

FIG. 6 illustrates a second embodiment of the invention wherein the safety element, here referred to by 116, consists of a braid of extremely thin, intertwined wires having a high electric conductivity.

Figure 3:
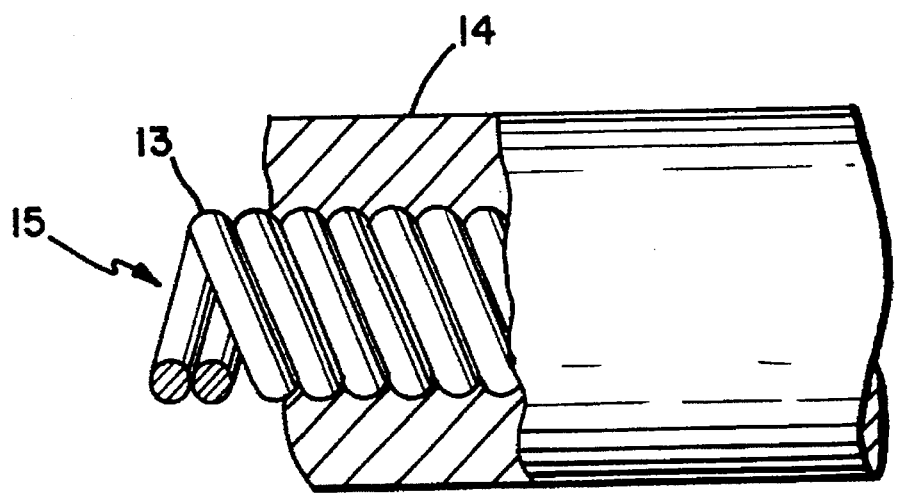
FIGS. 3 and 4 are fragmentary and partially sectioned views of a pulse transmitting lead with which the element of the invention is utilized according to a first embodiment thereof.
Figure 5:
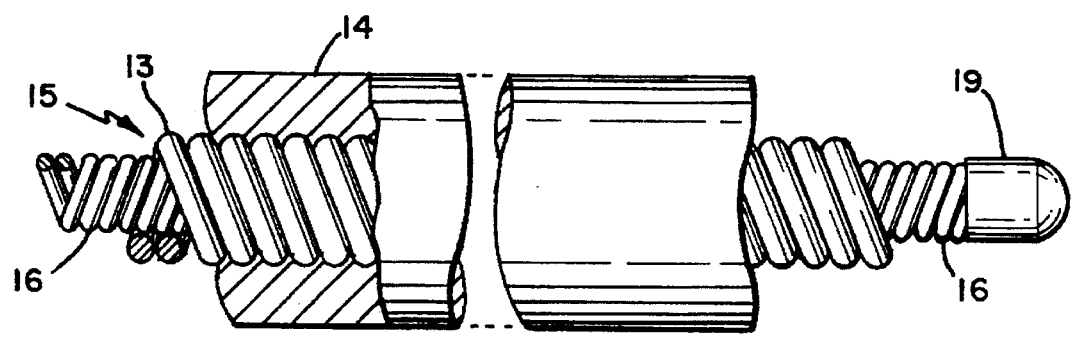
FIG. 5 is a partial section of the first embodiment of the invention provided with a rounded head intended to make it easier to introduce the safety element of the present invention into the pulse transmitting lead bore.

The modalities for installing and utilizing element 116 are exactly the same as for element 16 of FIGS. 3 and 5.

Both elements 16 and 116 are preferably provided with a rounded head, referred to by 19 and 119 in FIGS. 5 and 6, respectively, in order to facilitate the introduction thereof inside main coil 13.

As it will be self evident to persons skilled in the art the invention assures in a simple and not expensive way, safe operation of the pulse transmitting lead. Safety is provided even when the original implanted pacemaker has been substituted and cracks or microfractures may have impaired the physical structure and the electric continuity of the main coil originally implanted.

We claim:

1. In a heart stimulation apparatus of the type comprising a pacemaker, received in a subcutaneous pocket formed in the patient's chest, for generating stimulation pulses and a pulse transmitting lead (12) forwarding said pulses to the patient's heart, provided with a pin-jack (11) for connection to the pacemaker and a distal end (18) to be fixed to the endocardium of the right ventricle of said heart (HT) for transmitting thereto said stimulation pulses, wherein said pulse transmitting lead (12) has a coaxial, tubular structure consisting of an outer sheath (14) and an inner main coil (13) formed by one or more wires helically wound in closely tight turns, delimiting an inner bore (15) which bore, during first implantation of said pulse transmitting lead (12) in the patient's body, accommodates a thin, solid wire, mandrel (MN) that provides said pulse transmitting lead (12) the rigidity necessary to allow the pulse transmitting lead to be pushed from said subcutaneous pocket to the patient's heart (HT), wherein said distal end is adapted to be fixed to the heart's right ventricle, said mandrel (MN) being removed when said implantation is completed, the improvement comprising: a safety element (16, 116) insertable at the time of the necessary replacement of said pacemaker, comprising one or more electrically conductive very flexible wires wound to form a cylindrical body and sized to be fitted in said inner bore (15) of said main coil (13) for substantially continuous electrical contact with the inner surface of the main coil from the pin jack to the distal end of the pulse transmitting lead, capable of permanently assuring the electric continuity of said pulse transmittal lead even if cracks or micro-fractures have occurred therein.

2. The improved heart stimulation apparatus, wherein the one or more wires of the safety element are helically wound in tight turns to form a coil (16).

3. The improved heart stimulation apparatus of claim 1 wherein the one or more wires of the safety element comprise a plurality of very thin wires intertwined to form a flexible braid.

4. The improved heart stimulation apparatus of claim 1, wherein the safety element is provided with a rounded head (19, 119) to facilitate the introduction of said element (16, 116) in the bore (15) of said main coil (13).

* * * * *